United States Patent [19]
Krusko

[11] 3,981,306
[45] Sept. 21, 1976

[54] MULTILAYER ONE-PIECE DISPOSABLE DIAPERS

[75] Inventor: Evelyn H. Krusko, Newtown Square, Pa.

[73] Assignee: Scott Paper Company, Philadelphia, Pa.

[22] Filed: Aug. 11, 1975

[21] Appl. No.: 603,298

[52] U.S. Cl............................... 128/287; 128/284; 128/290 P
[51] Int. Cl.² ................... A16F 13/16; A41B 13/02
[58] Field of Search................ 128/284, 287, 290 R, 128/290 P, 296

[56] References Cited
UNITED STATES PATENTS

| 2,507,197 | 5/1950 | Matzdorf | 128/287 |
|---|---|---|---|
| 2,788,786 | 4/1957 | Dexter | 128/284 |
| 3,505,083 | 4/1970 | Schelhorn | 99/171 |
| 3,650,273 | 3/1972 | Schaar | 128/287 |
| 3,816,227 | 6/1974 | Schaar | 128/287 X |
| 3,848,599 | 11/1974 | Schaar | 128/287 |
| 3,885,568 | 5/1975 | Schaar | 128/287 |
| 3,926,189 | 12/1975 | Taylor | 128/287 |
| R26,151 | 1/1967 | Duncan et al. | 128/287 |

Primary Examiner—Aldrich F. Medbery
Attorney, Agent, or Firm—Martin L. Faigus; William J. Foley

[57] ABSTRACT

Multilayer, one-piece, disposable diapers according to this invention include a liquid-impervious backing layer adapted to encircle the thigh and waist regions of a wearer and an absorbent pad adapted to contact the wearer in the perineal region. The absorbent pad is bonded to the backing layer over a limited region disposed inwardly of at least two corners of the pad to permit marginal sections of the pad constituting at least about 50% of the total pad area to be moved independently of the backing layer.

21 Claims, 9 Drawing Figures

MULTILAYER ONE-PIECE DISPOSABLE DIAPERS

BACKGROUND OF THE INVENTION

1. Field of the Invention:

The present invention relates broadly to multilayer, onepiece, disposable diapers, and more particularly to diapers of the above type in which an absorbent pad is independently movable relative to a backing layer.

2. Description of the Prior Art:

Disposable diapers have become exceedingly popular in recent years. Commercially, the most successful disposable diapers have been of a multilayer, one-piece construction including a facing layer which is pervious to body fluids, an intermediate fluid-absorbing core for absorbing and retaining body fluids which pass through the facing layer and a liquid-impervious backing layer beneath the absorbent core for preventing body fluids from striking through the diaper. In these multilayer constructions the facing layer generally is intimately adhered to the backing layer at the side and end margins, and such intimate adherence prevents any significant relative movement between the various diaper components during use. In use the forces imposed upon these diapers in the thigh and waist encircling regions of a wearer are readily transmitted to the absorbent core through both the facing and backing layers. These forces can cause the absorbent core to shift out of desired conformation with the perineal region of the wearer to adversely affect the fluid-retaining capabilities of the diaper. Furthermore, due to the intimate adherence of the facing and backing layers at the side and end margins thereof the components of the diaper cannot easily be separated from each other. Separation of the diaper components is often desirable to permit disposal of flushable components in a conventional household toilet system.

The above-referred-to prior art diapers are not designed to permit manipulation of the absorbent core independently of the backing layer. Manipulation of the absorbent core may be desired to permit varying its geometry within the perenial region for accommodating the excretion characteristics of the wearer. For example, the excretion characteristics may vary with the age and sex of the wearer.

Representative multilayer, one-piece, disposable diapers which are subject to the above-described deficiencies are disclosed in U.S. Pat. Nos. Re. 26,151, issued to Duncan et al; 3,885,568, issued to Schaar; 3,816,227, issued to Schaar; 3,402,715, issued to Liloia et al; 2,788,786, issued to Dexter; 3,509,881, issued to Sabee and 2,788,003, issued to Morin.

U.S. Pat. No. 2,507,197, issued to Matzdorf, discloses a multilayer, one-piece diaper in which the absorbent material is in the form of separate fibrous layers that are intimately adhered to a backing layer through a liquid-impervious barrier sheet. This diaper does not permit manipulation of the absorbent layers independently of the backing layer.

Two-piece diaper systems have also been suggested in the prior art. These systems include a retaining garment which generally is adapted to be used over an extended period of time, and an absorbent pad which is removably secured to the retaining garment during use of the diaper. These two-piece diaper systems, in some cases, permit independent manipulation of the absorbent pad relative to the retaining garment. Also, forces imposed upon the retaining garment in regions encircling the thigh and waist regions of a wearer are not transmitted as readily to the absorbent pad as is the case with the above-described multilayer, one-piece diaper system.

The absorbent pads and retaining garments of the two-piece diaper systems are generally sold separately. This method of merchandising requires stores to stock various sizes of pads and various sizes of retaining garments. It has been found that an out-of-stock situation in one of the items generally has an adverse effect on the total volume sales of the entire diaper system. Accordingly, the two-piece diaper systems are considerably more difficult to successfully merchandise than the conventional multilayer, one-piece disposable diapers. Moreover, the retaining garments of the two-piece diaper systems have generally been highly durable due to the fact that they are intended to be utilized over an extended period of time. These highly durable retaining garments have been relatively expensive to manufacture, and therefore, the two-piece diaper systems employing such retaining garments do not easily compete in the low cost disposable diaper market. The diaper disclosed in U.S. Pat. No. 3,693,621, issued to Jarusik et al, is representative of the above-described two-piece diaper sytems.

It has also been suggested to employ separate inserts to be utilized with conventional multilayer, one-piece disposable diapers, as exemplified by the disclosure in U.S. Pat. No. 3,886,941. These inserts are sold separately from the disposable diapers, and are placed on the disposable diaper when needed for added absorbency. Such constructions do not in any way relate to multilayer, one-piece diaper constructions of the type which form the subject matter of the instant invention.

U.S. Pat. No. 3,505,083 discloses a two-ply wrapper for commestible products comprising a moisture absorbent layer selectively adhered at spaced points to a plastic film such that the two components can move relative to each other in the unbonded areas. This patent does not relate to disposable diapers of any type, and accordingly, does not relate to the multilayer, one-piece diaper constructions which form the subject matter of the instant invention.

SUMMARY OF THE INVENTION

The present invention resides in multilayer, one-piece disposable diapers which include a liquid-impervious backing layer and an absorbent pad bonded to the backing layer over a limited region disposed inwardly of at least two corners of the pad for permitting marginal sections of the pad which constitute at least about 50% of the total pad area to move independently of the backing layer.

The term one-piece, as used throughout this application to characterize multilayer diapers, refers to a diaper which is manufactured and sold with its separate layers integrated into a single unit by suitable bonding means, and, with the possible exception of fastening means for retaining the diaper about a wearer's torso, does not require the inclusion or attachment of additional components to render it usable. The bonding means for retaining the layers in a one-piece construction need not bond each layer to an adjacent layer.

The term disposable, as used throughout this application to characterize diapers, refers to diapers which are adapted for a single use, i.e., they are not intended to be washed and reused.

The limited adherence between the absorbent pad and backing layer, as described earlier, provides sufficient independence of movement between said absorbent pad and backing layer to permit the desired placement of the pad within the perineal region of a wearer while at the same time permitting substantially independent placement of the backing layer in close-fitting relationship with the thigh and waist regions of the wearer. Moreover, the above-described structure prevents the forces acting upon the thigh and waist confining regions of the backing layer from adversely affectng either the integrity of the absorbent pad, or the conformation of the absorbent pad within the perineal region of the wearer.

In the preferred embodiments of this invention the absorbent pad is bonded to the backing layer through either a single adhesive line, which may be either continuous or discontinuous, or through a single spot bond. Most preferably the absorbent pad is retained to the backing layer through a single spot bond located at or near the center of the pad to permit maximum independence of movement between the absorbent pad and the backing layer.

The absorbent pad can be rectangular, or shaped to have a medial region of a narrower transverse dimension than forward and/or or rearward regions thereof. A preferred shaped pad has a substantially hour glass-shaped configuration which generally conforms to the contour of the perineal region in which it is retained.

If the desired adhesive tabs, or other fastening means, can be associated with the absorbent pad so that said pad can be secured in its desired position about the wearer prior to securing the backing layer around the thigh and waist regions of the wearer. Adhesive fastening means, or other similar fastening means, can optionally be included on the backing layer to secure said backing layer about the torso of the wearer with the absorbent pad encased within the backing layer for preventing leakage of body fluids from within the confines of the diaper.

Other object and advantages of this invention will become apparent upon reading the detailed description which follows, taken in conjunction with the drawings.

DESCRIPTION OF THE PREFERRED EMBODIMENTS OF THE INVENTION

Figure 1:
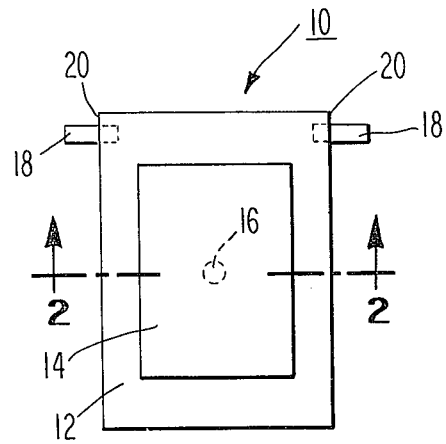
FIG. 1 is a plan view of a multilayer, one-piece disposable diaper according to this invention.

Referring to FIG. 1, a multilayer, one-piece, disposable diaper 10 according to this invention includes a backing layer 12 and an absorbent pad 14 bonded to the backing layer by a spot bond 16 located at the center of the absorbent pad. Except for the spot bond 16 between the absorbent pad 14 and the backing layer 12, the absorbent pad is free and not otherwise adhered to, or confined by the backing layer when the diaper is in a flat, unfolded condition. Thus, referring to FIG. 1, the marginal sections of the pad 14 extending inwardly from all four corners thereof can be manipulated independently of the backing layer 12 to obtain the desired conformation of the absorbent pad 14 within the perineal region of a wearer. The desired conformation may vary depending upon the size, sex and age of the wearer. For example, a male infant tends to initially direct fluid flow toward the forward region of the absorbent pad. Accordingly, when the diaper is intended to be used by a male infant, it may be desirable to fold a front margin of the pad inwardly to provide a double thickness of absorbent material adjacent the forward region of the diaper. Also, for some applications, it may be desirable to fold side margins of the pad inwardly to increase the absorbent capacity along the entire longitudinal extent of said pad. The choice of configuration can be left to the individual that is placing the diaper 10 on the wearer.

Referring to FIG. 1, adhesive tabs 18 are located at opposite sides of the diaper adjacent rear corners 20 of the backing layer 12. The use of such adhesive tabs is optional in the diaper constructions of this invention, but is preferred since it eliminates the need for employing separate fastening means, such as pins, to fix the diaper about the torso of the wearer.

Figure 2:
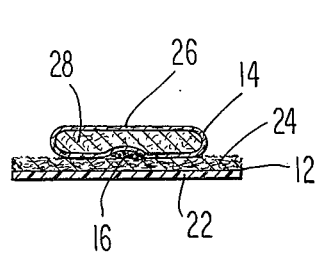
FIG. 2 is a transverse sectional view taken along line 2—2 of FIG. 1.

Referring specifically to FIGS. 1 and 2, the backing layer 12 of the diaper 10 is substantially rectangular in plan view, and has sufficient longitudinal and transverse dimensions for encircling the thigh and waist regions of a wearer. The rectangular configuration of the backing layer 12 is preferred since it permits the side margins thereof to be gathered to varying degrees to provide a conforming fit about a wide variety of thigh sizes. Although the rectangular configuration of the backing layer is preferred, the specific shape of the backing layer can be varied in accordance with the broadest aspects of this invention.

The backing layer 12 is liquid-impervious, and preferably includes a outer plastic sheet 22 and an inner, soft sheet 24 bonded to the outer sheet. The plastic sheet 22 can be formed of any conventional plastic material normally employed in disposable diapers; such materials being well known to those skilled in the art. For example, thin, flexible, plastic film such as polyethylene, polypropylene and polyvinylchloride having a thickness in the range of from about 0.5 mils to about 2.0 mils is satisfactory for use in this invention.

The inner sheet 24 of the backing layer 12 preferably is formed of a soft, fibrous material, and is adapted to contact the wearer to prevent chaffing of the skin. If desired, the sheet 24 can also be absorbent to increase the total fluid retaining capacity of the diaper. However, in the preferred embodiments of this invention the primary absorbent component of the diaper, by weight, is the absorbent pad 14.

Typically, when the inner sheet 24 is a fibrous structure, it may be formed by either a wet-forming or a dry-forming process. Preferably, the sheet 24 is comprised predominately, or solely of short cellulosic fibers of a papermaking length less than ¼ inch (e.g., woodpulp or cotton linters) to provide a soft, low cost construction. However, it is within the scope of this invention to form the sheet 24 entirely of textile-length fibers over ¼ inch in length. Such textile webs can be formed by well known processes, such as, for example, carding and air-laying processes.

Referring again to FIGS. 1 and 2, the absorbent pad 14 is of a rectangular configuration, having shorter transverse and longitudinal dimensions than the backing layer 12. Accordingly, even if the absorbent pad 14 is not folded, or otherwise manipulated, prior to placing the diaper on a wearer, said absorbent pad will still be encased within the backing layer when the diaper is placed on the wearer to prevent the leakage of body fluids from within the confines of said diaper.

The absorbent pad 14 includes a fluid-permeable outer cover sheet 26 surrounding and enclosing an absorbent core 28. The fluid-permeable cover sheet 26 may be either hydrophilic or hydrophobic. However, the cover sheet should be soft, flexible and substantially non-adherent to the skin of a wearer when either dry or wet. Also, the primary characteristic necessary for the cover sheet 26 is that it pass fluids rapidly into the interior absorbent core 28. Dry-formed webs of rayon or polyester fibers have been suitable for use as the cover sheet 26. However, this invention is not limited to the use of any particular material for the cover sheet 26, it being understood that other materials which permit body fluids to pass through it can be utilized within the broadest aspects of this invention.

If desired, the absorbent pad 14 can be formed from a plurality of plies of creped cellulosic wadding, or other absorbent sheet material, which are adhered to each other in a stacked relationship. In such a construction a separate cover sheet is not requried. Alternatively, the absorbent pad 14 can be provided by a loosely compacted batt of substantially individualized fibers which is stabilized by an adhesive coating disposed over the outer periphery thereof. A pad of the latter type is disclosed in U.S. Pat. No. 3,395,201, issued to Kalwaites.

If desired, the pad 14 can include absorbent polymers such as insoluble hydrophilic homopolymers and copolymers which gel upon the absorption of urine.

Figure 3:
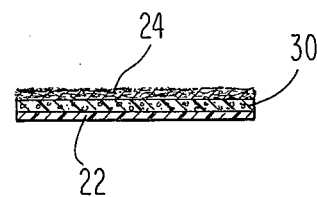
FIG. 3 is a transverse sectional view similar to FIG. 2, but showing an alternative variant of a backing layer with the absorbent pad omitted.

Referring to FIG. 3, an alternative backing layer construction which can be used in the disposable diapers of this invention includes a foam layer 30 interposed between the outer plastic sheet 22 and the inner sheet 24. The outer plastic sheet 22 and the inner sheet 24 are of the same construction as described above in connection with the backing layer shown in FIG. 2. The foam layer 30 can be of any suitable material which is resilient, soft and stretchable. Preferably, the foam layer is an elastomeric, wet-stable layer of the type disclosed in U.S. Pat. application Ser. No. 519,415, filed on Oct. 31, 1974, (now U.S Pat. No. 3,916,900) and assigned to Scott Paper Company. The preferred elastomeric, wet-stable foam layer is a polyurethane foam; however, for further details relating to the preferred foam materials utilizable in this invention reference should be had to the U.S. Pat. NO. 519,415 which is herein incorporated by reference.

The particular liquid-impervious backing layer which is employed does not constitute a limitation on the broadest aspects of the instant invention. If desired, the backing layer 12 could include elasticized side and/or end margins to enhance the fit of said backing layer about the thigh and/or waist regions of the wearer.

Figure 4:
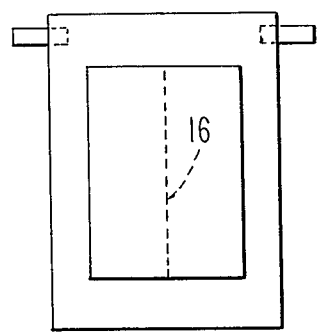
FIG. 4 is a plan view of a second embodiment of a disposable diaper according to this invention.
Figure 5:
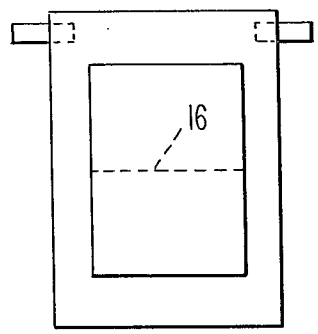
FIG. 5 is a plan view of a third embodiment of a disposable diaper according to this invention.
Figure 6:
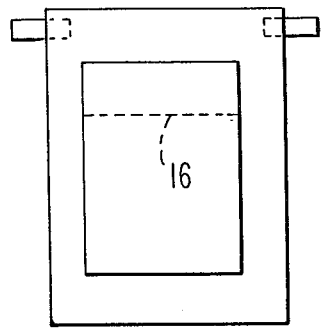
FIG. 6 is a plan view of a fourth embodiment of a disposable diaper according to this invention.
Figure 7:
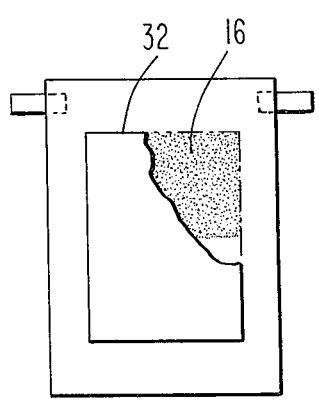
FIG. 7 is a plan view of a fifth embodiment of a disposable diaper according to this invention.

Referring to FIGS. 4–7, several alternative diaper constructions are shown which differ from each other, and from the diaper shown in FIG. 1, in the specific location of the adhesive bond 16 which is employed to retain the absorbent pad to the backing layer. In FIG. 4 the bonded zone 16 is in the form of a discontinuous line located along the longitudinal axis of the absorbent pad 14. In FIG. 5 the bonded zone 16 is disposed in a discontinuous line along the transverse axis of the absorbent pad 14. In FIG. 6 the bonded zone is disposed in a discontinuous line extending transversely of the absorbent pad 14 and rearwardly of the transverse center line of said pad. In FIG. 7 the bonded zone is disposed substantially uniformly over the rear half of the pad disposed between the transverse center line and rear margin 32. In all of these diaper constructions at least about 50% of the pad area extending inwardly from the margins thereof can be manipulated completely independently of the backing layer to permit separate conformation of the pad within the perineal region as the diaper is placed upon a wearer.

Figure 8:
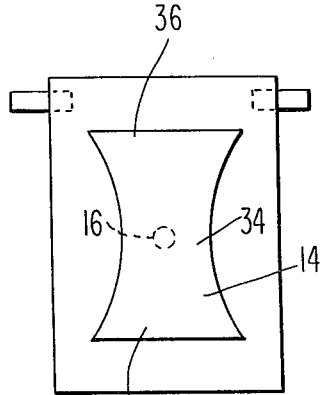
FIG. 8 is a plan view of a sixth embodiment of a disposable diaper according to this invention.

Referring to FIG. 8, a further embodiment of a disposable diaper 10 includes an absorbent pad 14 having a contoured configuration. Preferably the contoured absorbent pad 14 is of an hourglass shape in which the transverse dimension of medial region 34 is narrower than the transverse dimensions of forward and rearward regions 36 and 38, respectively. Other contours can be employed. For example, the absorbent pad could be T-shaped with the forward or rearward region constituting the head of the T and the remainder of the pad constituting the stem of the T. In such a construction the medial region of the pad is narrower than only the forward or rearward region, depending upon whether the head of the T is the forward or rearward region of the absorbent pad.

In the embodiment shown in FIG. 8 a single spot bond 16 located at the center of the absorbent pad 14 is employed to retain said absorbent pad to the backing layer 12. The hourglass shape of the absorbent pad provides a contour which generally conforms to the perineal region of the wearer, and accordingly, only a limited readjustment of the shape of the pad may be desired when placing the diaper on a wearer. The limited adherence of the absorbent pad to the backing layer in the FIG. 8 embodiment will prevent excessive force transmission from the backing layer to the absorbent pad 14 during use of said diaper. This avoids the deleterious effects associated with excessive force transmission as described earlier in connection with the prior art multilayer, one-piece diaper constructions.

Figure 9:
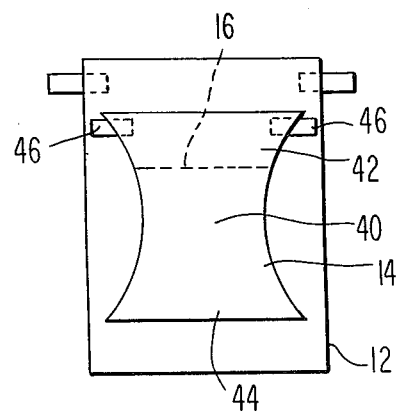
FIG. 9 is a plan view of an additional variant employing the concepts of this invention.

Referring to FIG. 9, an additional variant of a disposable diaper employing the concepts of this invention includes a substantially hourglass-shaped absorbent pad 14 having a medial region 40 of a narrower transverse dimension than forward and rearward regions 42 and 44, respectively. The forward and rearward regions are shown as being slightly wider than the corresponding regions of the hourglass-shaped pad in FIG. 8 for permitting the absorbent pad 14 to be positioned and attached about the torso of a wearer independently of the backing layer 12. This independent attachment of the absorbent pad 14 about the torso of a wearer is achieved by providing adhesive tabs 46, or other suitable fastening means, at opposite sides of said pad. In the embodiment shown in FIG. 9 the bonded zone 16 is in the form of a transverse, discontinuous line located rearwardly of the transversely extending axis of the pad to permit a major portion of the forward section of the pad to be lifted over the front of a wearer for attachment to the rear section of the pad by the tabs 46. The location of this bonded zone can be varied within wide limits, provided that the particular location permits sufficient manipulation of the absorbent pad so that said pad can be secured about the torso of a wearer independently of the backing layer 12. When the pad 14 is independently secured within the perineal region of the wearer a close conformance with the perineal region will be maintained, regardless of the forces imposed upon it through the backing layer 12 during use of the diaper.

The location at which the absorbent pad 14 can be adhered to the backing layer 12 in the disposable diapers of this invention can be varied within wide limits. With respect to the broadest aspects of this invention, any bonding location is acceptable which permits the marginal sections of the pad constituting at least 50% of the total pad area to be moved completely independently of the backing layer. For example, the bonded zone may be in the form of a discontinuous line, as described above in connection with FIGS. 4–6, or alternatively the line can be continuous. Also, the adhesive can be applied in a liquid state to either the backing layer 12 or the absorbent pad 14. Alternatively, the adhesive can be in the form of a two-sided adhesive tape. Also, in place of a single spot bond as disclosed in FIGS. 1 and 8, a plurality of spot bonds can be employed.

The use of integral fastening means, such as adhesive tape, secured to the backing layer 12 is optional in accordance with the broadest aspects of this invention. It is understood that any conventional adhesive tape could be employed to secure the diaper about the torso of a wearer, and that the particular tape utilized does not form a part of the present invention per se. Therefore no detailed description of tape fasteners will be offered here.

While the invention has been shown and described by reference to the preferred embodiments thereof, it is to be understood that various changes, modifications and/or substitutions may be made therein without departing from the spirit of this invention. Accordingly, it is the intention that the instant invention be limited only by the scope of the appended claims.

What is claimed is:

1. A multilayer, one-piece, disposable diaper comprising a liquid-impervious backing layer having sufficient longitudinal and transverse dimensions for encircling the thigh and waist regions of a wearer, a fluid-absorbent pad adapted to be disposed in the perineal region of the wearer for receiving and retaining body fluids, said pad constituting the primary absorbent component, by weight, of the diaper and being superposed on said backing layer and means for providing adjustable movement between said backing layer and said pad comprising bonding means securing the fluid-absorbent pad to the backing layer over only a limited region disposed inwardly of at least two corners of said pad for permitting marginal sections of the pad which constitute at least 50% of the total pad area to move independently of the backing layer.

2. The disposable diaper according to claim 1, wherein said absorbent pad includes a central core of fluid-absorbent material disposed within a fluid-pervious cover sheet.

3. The disposable diaper according to claim 1, wherein said absorbent pad has a medial region of a narrower transverse dimension than forward and/or rearward regions thereof.

4. The disposable diaper according to claim 1, wherein said absorbent pad is bonded to said backing layer with a pressure sensitive adhesive.

5. The disposable diaper according to claim 1, wherein said limited bonded region is provided by a single spot bond located inwardly of all marginal edges of the pad.

6. The disposable diaper according to claim 5, wherein said single spot bond is located at the center of the absorbent pad.

7. The disposable diaper according to claim 1, wherein said backing layer comprises an outer sheet of a liquid-impervious material and an inner sheet composed of a soft, fibrous material.

8. The disposable diaper according to claim 1, wherein said backing layer is provided with adhesive closure means for securing the diaper about a wearer.

9. The disposable diaper according to claim 1, wherein the absorbent pad has smaller longitudinal and transverse dimensions than the backing layer.

10. The disposable diaper according to claim 1, wherein said limited bonded region is along a line which either defines or intersects the horizontal or vertical center line of the absorbent pad.

11. The disposable diaper according to claim 10, wherein said bonding line is along the vertical center line of the absorbent pad.

12. The disposable diaper according to claim 10, wherein said bonding line is along the horizontal center line of the absorbent pad.

13. The disposable diaper according to claim 10, wherein said bonding line is a horizontal line disposed rearwardly of the horizontally extending center line of the absorbent pad.

14. A multilayer, one-piece disposable diaper comprising a liquid-impervious backing layer having sufficient longitudinal and transverse dimensions for encircling the thigh and waist regions of a wearer, a fluid-absorbent pad adapted to be disposed in the perineal region of the wearer for receiving and retaining body fluids, said pad having a longitudinal dimension provided by opposed end margins and being superposed on the backing layer with its end margins disposed on opposite sides of the transverse medial line of the backing layer and means for providing adjustable movement between said backing layer and said pad comprising bonding means securing the pad to the backing layer over only a limited region disposed inwardly of at least two corners of said pad which are disposed on opposite sides of the transverse medial line of the backing layer for permitting marginal sections of the pad constituting at least about 50% of the total pad area to move independently of the backing layer.

15. The disposable diaper according to claim 14, wherein said fluid-absorbent pad constitutes the primary absorbent component, by weight, of the diaper.

16. The disposable diaper according to claim 14, wherein said limited bonded region is provided by a single spot bond located inwardly of all marginal edges of the pad.

17. The disposable diaper according to claim 16, wherein said single spot bond is located at the center of the absorbent pad.

18. The disposable diaper according to claim 14, wherein said backing layer comprises an outer sheet of a liquid-impervious material and an inner sheet composed of a soft, fibrous material.

19. The disposable diaper according to claim 14, wherein said bonding means is a line along the vertical center line of the absorbent pad.

20. The disposable diaper according to claim 14, wherein said bonding means is a line along the horizontal center line of the absorbent pad.

21. The disposable diaper according to claim 14, wherein said bonding means is a horizontal line disposed rearwardly of the horizontally extending center line of the absorbent pad.

* * * * *